(12) United States Patent
Munchhof

(10) Patent No.: US 7,199,123 B2
(45) Date of Patent: Apr. 3, 2007

(54) PYRAZINE COMPOUNDS AS TRANSFORMING GROWTH FACTOR (TGF) COMPOUNDS

(75) Inventor: Michael J. Munchhof, Salem, CT (US)

(73) Assignee: Pfizer Inc., New York, NY (US)

( * ) Notice: Subject to any disclaimer, the term of this patent is extended or adjusted under 35 U.S.C. 154(b) by 272 days.

(21) Appl. No.: 10/798,198

(22) Filed: Mar. 10, 2004

(65) Prior Publication Data

US 2004/0180905 A1 Sep. 16, 2004

Related U.S. Application Data

(60) Provisional application No. 60/453,784, filed on Mar. 11, 2003.

(51) Int. Cl.
*A61K 31/4965* (2006.01)
*C07D 401/00* (2006.01)
*C07D 403/00* (2006.01)
*C07D 405/00* (2006.01)
*C07D 409/00* (2006.01)

(52) U.S. Cl. .................... 514/255.05; 514/255.06; 544/405; 544/406

(58) Field of Classification Search .............. None
See application file for complete search history.

(56) References Cited

U.S. PATENT DOCUMENTS

| | | | | |
|---|---|---|---|---|
| 3,119,742 A | 1/1964 | Heimlich et al. | ............. | 167/82 |
| 3,492,397 A | 1/1970 | Peters et al. | ................. | 424/20 |
| 3,538,214 A | 11/1970 | Polli et al. | ..................... | 424/19 |
| 4,060,598 A | 11/1977 | Groppenbächer et al. | ..... | 424/33 |
| 4,173,626 A | 11/1979 | Dempski et al. | .............. | 424/19 |

FOREIGN PATENT DOCUMENTS

| | | |
|---|---|---|
| EP | 1156045 | 11/2001 |
| WO | WO0248152 | 6/2002 |
| WO | WO0262776 | 8/2002 |
| WO | WO0262787 | 8/2002 |
| WO | WO0304472 | 1/2003 |
| WO | WO0304475 | 1/2003 |
| WO | WO0393297 | 11/2003 |

OTHER PUBLICATIONS

Vippagunta et al, "Crystalline Solids" Advanced Drug Delivery Reviews, vol. 48, pp. 3-26 (2001).*
Al-Dabbagh and Smith, "Species differences in oxidative drug metabolism: some basic considerations." Archives of toxicology. Supplement. Archiv fur Toxikologie. supplement, vol. 7, pp. 219-231 (1984).*
Hans Bundgaard, Design of Prodrugs, p. 1. © 1985 Elsevier Science Publishers.*
Richard B. Silverman, The Organic Chemistry of Drug Design and Drug Action, pp. 352-400. © 1992 Academic Press, Inc.*
De Meester, J.W.G., et al., "Synthesis of 3-Alkyl-6-Phenyl-4(3H)-pteridinones and their 8-Oxides. Potential Substrates of Xanthine Oxidase", J. Heterocyclic Chem. vol. 24, No. 4, pp. 1109-1116 (1987).
Laping, N.J., et al., "Inhibition of Transforming Growth Factor (TGF)-β1-induced Extracellular Matrix with a Novel Inhibitor of the TGF-β Type I Receptor Kinase Activity: SB-431542", Molecular Pharmacology, vol. 62, No. 1, pp. 58-64 (2002).

* cited by examiner

*Primary Examiner*—Zachary C. Tucker
(74) *Attorney, Agent, or Firm*—Eric J. Baude; Rosanne Goodman; Charles W. Ashbrook

(57) ABSTRACT

Novel pyrazine compounds, including derivatives thereof, to intermediates for their preparation, to pharmaceutical compositions containing them and to their medicinal use are described. The compounds of the present invention are potent inhibitors of transforming growth factor ("TGF")-β signaling pathway. They are useful in the treatment of various TGF-related disease states including, for example, cancer and fibrotic diseases.

18 Claims, No Drawings

PYRAZINE COMPOUNDS AS TRANSFORMING GROWTH FACTOR (TGF) COMPOUNDS

RELATED APPLICATIONS

This application claims benefit of priority under 35 U.S.C. 119(e) to U.S. Provisional Application No. 60/453,784, filed Mar. 11, 2003, which is incorporated herein in its entirety by reference.

BACKGROUND OF THE INVENTION

The present invention relates to novel pyrazine compounds, including derivatives thereof, to intermediates for their preparation, to pharmaceutical compositions containing them and to their medicinal use. The compounds of the present invention are potent inhibitors of the transforming growth factor ("TGF")-β signaling pathway. They are useful in the treatment of TGF-β related disease states including, for example, cancer and fibrotic diseases.

SUMMARY OF THE INVENTION

The invention provides a compound of formula (I):

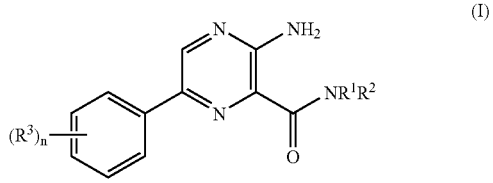

or a pharmaceutically acceptable salt, prodrug, hydrate or solvate thereof where:

$R^1$ is H;

$R^2$ is a substituted or unsubstituted $(C_1-C_8)$alkyl, $(C_3-C_9)$cycloalkyl, $(C_3-C_9)$aryl, $(C_3-C_9)$ heteroaryl, amide, amino, $(C_3-C_8)$hydroxyalkyl, $(C_3-C_9)$heterocycloalkyl, $(C_3-C_9)$aryl$(C_1-C_8)$alkyl, amino$(C_1-C_8)$alkyl, amido$(C_1-C_8)$alkyl; or $R^1$ and $R^2$ taken together with the nitrogen to which they are attached form a substituted or unsubstituted heterocycloalkyl or heteroaryl;

$R^3$ is independently selected from the group consisting of H, $(C_1-C_8)$alkyl, halo, $(C_1-C_8)$alkoxy, sulfonyl, cyano, and keto; preferably, H, bromo, chloro, cyano, methoxy, $(C_1-C_8)$alkyl-$SO_2$—, and $(C_1-C_8)$alkylC(=O)—;

n is an integer from 0–5; preferably, 0–4; more preferably, 0–1, with the proviso that the compound is not 3-amino-6-phenyl-pyrazine-2-carboxylic acid butylamide or 3-amino-6-phenyl-pyrazine-2-carboxylic acid (2-hydroxy-ethyl)-amide.

The invention also provides a compound of formula (II):

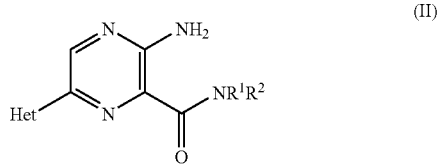

or pharmaceutically acceptable salt, prodrug, hydrate or solvate thereof where:

$R^1$ is H;

$R^2$ is a substituted or unsubstituted $(C_3-C_8)$hydroxyalkyl, $(C_3-C_9)$ cycloalkyl, $(C_3-C_9)$heterocycloalkyl, $(C_3-C_9)$heteroaryl, amino$(C_1-C_8)$alkyl, $(C_3-C_9)$aryl$(C_1-C_8)$ alkyl, or amido$(C_1-C_8)$alkyl; or $R^1$ and $R^2$ taken together with the nitrogen to which they are attached form a substituted or unsubstituted heterocycloalkyl or heteroaryl group;

Het is a substituted or unsubstituted heterocyclyl or heteroaryl group containing at least one heteroatom selected from N, O and S; preferably, a substituted or unsubstituted $(C_5-C_{10})$heterocyclyl or heteroaryl group containing at least one heteroatom selected from N, O and S; more preferably, a substituted or unsubstituted furanyl, thienyl, pyridyl, or benzofuranyl group.

The invention further provides a compound of formula (III):

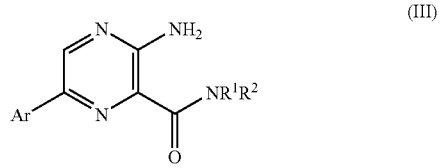

or a pharmaceutically acceptable salt, prodrug, hydrate or solvate thereof where:

$R^1$ is H;

$R^2$ is a substituted or unsubstituted $(C_3-C_8)$hydroxyalkl; preferably, a substituted or unsubstituted $(C_1-C_5)$hydroxyalkyl; more preferably, a substituted or unsubstituted $(C_3-C_5)$hydroxyalkyl;

Ar is a substituted or unsubstituted $(C_3-C_9)$aryl group; preferably a substituted or unsubstituted naphthyl group, with the proviso that the compound is not 3-amino-6-phenyl-pyrazine-2-carboxylic acid butylamide or 3-amino-6-phenyl-pyrazine-2-carboxylic acid (2-hydroxy-ethyl)-amide.

Suitable substituents for a compound of formula (I), (II) or (III), each as set forth above, are as defined below and also include those set forth in the Examples below. Preferably, the substituent is one as set forth in the Examples below. Furthermore, any two substituents on adjacent carbons can be taken together with the atoms to which they are attached to form a carbocyclic, non-aromatic or aromatic moiety which optionally contains at least one heteroatom selected from the group consisting of N, O and S. Still further, a substituent can be further substituted (e.g., benzyl-piperazine). A compound of the invention may contain more than one substituent.

The invention still further provides a pharmaceutical composition comprising a compound of the invention and a pharmaceutically acceptable carrier, each as described herein.

The invention further provides a method of preparation of a compound of the invention.

The invention also provides a method of preventing or treating a TGF-related disease state in a mammal (animal or human) comprising the step of administering a therapeutically effective amount of a compound of the invention to the animal or human suffering from the TGF-related disease state, each as described herein. In a preferred embodiment, the TGF-related disease state is selected from the group consisting of cancer, glomerulonephritis, diabetic nephropathy, hepatic fibrosis, pulmonary fibrosis, intimal hyperplasia and restenosis, scleroderma, and dermal scarring.

A compound of the invention can be used in the manufacture of a medicament for the prophylactic or therapeutic treatment of a TGF-related disease state in a mammal (animal or human).

DEFINITIONS

As used herein, the article "a" or "an" refers to both the singular and plural form of the object to which it refers unless indicated otherwise.

As used herein, the term "alkyl," as well as the alkyl moieties of other groups referred to herein (e.g., alkoxy) refers to a linear or branched saturated hydrocarbon (e.g., methyl, ethyl, n-propyl, isopropyl, n-butyl, iso-butyl, secondary-butyl, tertiary-butyl).

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl).

As used herein, the term "halogen" or "halo" refers to includes fluoro, chloro, bromo or iodo or fluoride, chloride, bromide or iodide.

As used herein, the term "halo-substituted alkyl" or "haloalkyl" refers to an alkyl radical, as set forth above, substituted with one or more halogens, as set forth above, including, but not limited to, chloromethyl, dichloromethyl, fluoromethyl, difluoromethyl, trifluoromethyl, and 2,2,2-trichloroethyl.

As used herein, the term "alkenyl" refers to a linear or branched hydrocarbon chain radical containing at least two carbon atoms and at least one double bond. Examples include, but are not limited to, ethenyl, 1-propenyl, 2-propenyl (allyl), iso-propenyl, 2-methyl-1-propenyl, 1-butenyl, and 2-butenyl.

As used herein, the term "alkynyl" refers to a linear or branched hydrocarbon chain radical having at least one triple bond including, but not limited to, ethynyl, propynyl, and butynyl.

As used herein, the term "carbonyl" refers to a >C=O moiety. Alkoxycarbonylamino (i.e. alkoxy(C=O)—NH—) refers to an alkyl carbamate group. The carbonyl group is also equivalently defined herein as (C=O).

As used herein, the term "phenyl-[(alkyl)-N]—(C=O)—" refers to a N.N'-disubstituted amide group of the formula

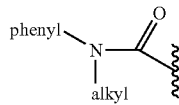

As used herein, the term "aryl" refers to an aromatic radical such as, for example, phenyl, naphthyl, tetrahydronaphthyl, and indanyl.

As used herein, the term "heteroaryl" refers to an aromatic group containing at least one heteroatom selected from O, S and N. For example, heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl.

As used herein, the term "heterocycle", "heterocyclyl" or "heterocyclic" refers to a saturated, unsaturated or aromatic $C_3$–$C_{20}$ mono-, bi- or polycyclic group containing at least one heteroatom selected from N, O, and S. Examples of heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxcithiazinyl, indolinyl, isoindolinyl, quincuclidinyl, chromanyl, isochromanyl, benzocazinyl, and the like. Examples of monocyclic saturated or unsaturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl.

The term "oxo" refers to a double bonded oxygen moiety, i.e., =O.

As used herein, the term "pharmaceutically acceptable acid addition salt" refers to non-toxic acid addition salts, ie., salts derived from pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [ie., 1,1'-methylene-bis-(2-hydroxy-3-naphthoate)]salts.

As used herein, the term "pharmaceutically acceptable base addition salt" refers to non-toxic base addition salts, i.e., salts derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

As used herein, the term "suitable substituent", "substituent" or "substituted" refers to a chemically and pharmaceutically acceptable functional group, i.e., a moiety that does not negate the inhibitory and/or therapeutic activity of the inventive compounds. Such suitable substituents may be routinely selected by those skilled in the art. Illustrative examples of suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, —O—($C_1$–$C_6$) alkyl, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Those skilled in the art will appreciate that many substituents can be substituted by additional substituents.

As used herein, the term "TGF-related disease state" refers to any disease state mediated by the production of TGF-β.

DETAILED DESCRIPTION OF THE INVENTION

A compound of the invention may be prepared according to the Schemes and Examples as described below. Unless otherwise indicated, all variables in the reaction schemes and discussion that follow are each as defined herein.

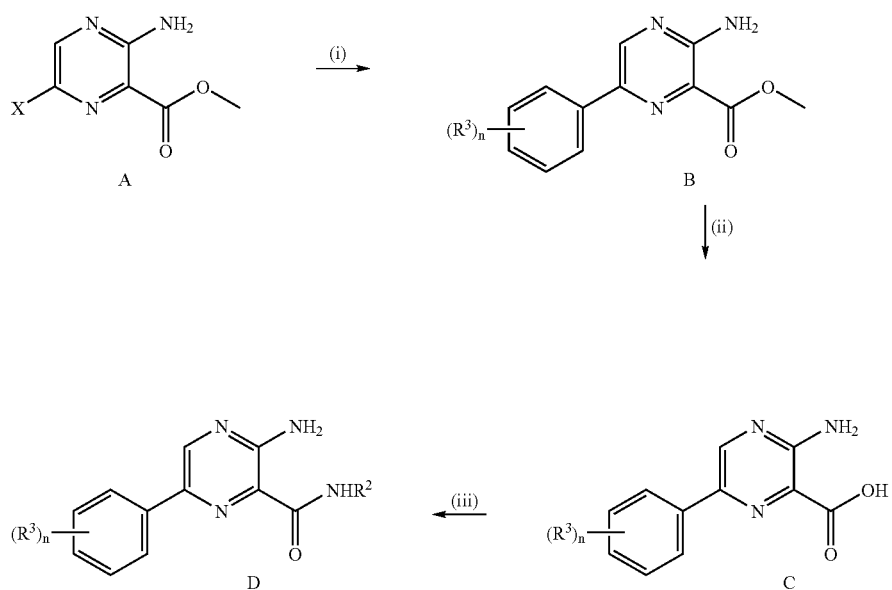

In reaction (i) of Scheme 1, compound A is reacted with a boronic acid of formula

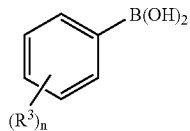

in the presence of a catalyst, such as, for example, Pd(dppb)Cl$_2$, Pd(PPh$_3$)$_4$, or bis-(diphenylphosphino)ferrocene/palladium acetate, in an aprotic solvent, such as dimethylformamide, at a temperature between about 30° C. to about 130° C., preferably, about 90° C., and for a time period between about 2 hours to about 24 hours, preferably, about 12 hours, to form compound B. In reaction (ii) of Scheme 1, compound B is then subjected to hydrolysis conditions to form the corresponding acid of compound C. In reaction (iii) of Scheme 1, compound C is reacted with amine R$^2$NH$_2$ to form the amide compound D.

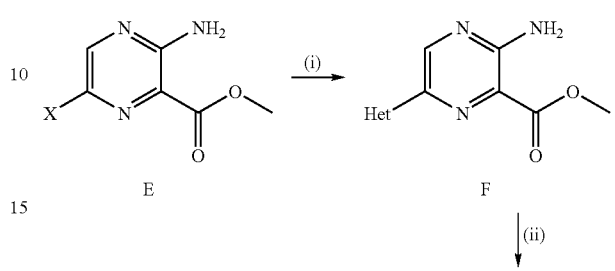

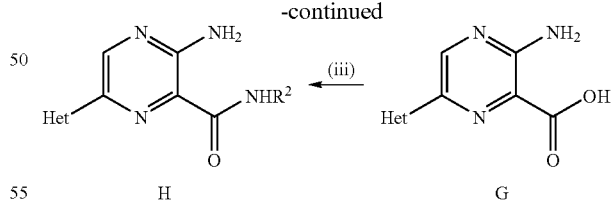

In reaction (i) of Scheme 2, compound E is reacted with boronic acid of formula Het-B(OH)$_2$ in the presence of a catalyst, such as, for example, Pd(dppb)Cl$_2$, Pd(PPh$_3$)$_4$, or bis-(diphenylphosphino)ferrocene/palladium acetate, in an aprotic solvent, such as dimethylformamide, at a temperature between about 30° C. to about 130° C., preferably, about 90° C., and for a time period between about 2 hours to about 24 hours, preferably, about 12 hours, to form compound F. In reaction (ii) of Scheme 2, compound F is then subjected to hydrolysis conditions to form the corresponding acid of compound G. In reaction (iii) of Scheme 2, compound G is reacted with amine $R^2NH_2$ to form the amide compound H.

All pharmaceutically acceptable salts, prodrugs, hydrates and solvates of a compound of formulae (I), (II), or (III) are encompassed by the present invention.

A compound of the invention which is basic in nature is capable of forming a wide variety of different salts with various inorganic and organic acids. Although such salts must be pharmaceutically acceptable for administration to animals and humans, it is often desirable in practice to initially isolate a compound of the invention from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained.

The acids which can be used to prepare the pharmaceutically acceptable acid addition salts of the base compounds of this invention are those which form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [ie., 1,1'-methylene-bis-(2-hydroxy-3-naphthoate)] salts.

A compound of the invention which is also acidic in nature, e.g., contains a COOH or tetrazole moiety, is capable of forming base salts with various pharmacologically acceptable cations. Examples of such pharmaceutically acceptable base addition salts include the alkali metal or alkaline-earth metal salts and particularly, the sodium and potassium salts. These salts can be prepared by conventional techniques. The chemical bases which can be used as reagents to prepare the pharmaceutically acceptable base addition salts of this invention are those which form non-toxic base salts with the herein described acidic compounds of the invention. These non-toxic base salts include salts derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Isotopically-labeled compounds are also encompassed by the present invention. As used herein, an "isotopically-labeled compound" refers to a compound of the invention including pharmaceutical salts, prodrugs thereof, each as described herein, in which one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$ $^{18}O$, $^{17}O$, $^{31}P$, $^{32}P$, $^{35}S$, $^{18}F$, and $^{36}Cl$ respectively.

By isotopically-labeling a compound of the present invention, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds of the invention, including pharmaceutical salts, prodrugs thereof, can be prepared by any means known in the art.

Stereoisomers (e.g., cis and trans isomers) and all optical isomers of a compound of the invention (e.g., R and S enantiomers), as well as racemic, diastereomeric and other mixtures of such isomers are contemplated by the present invention.

The compounds, salts, prodrugs, hydrates and solvates of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The present invention also includes atropisomers of the present invention. Atropisomers refer to compounds of the invention that can be separated into rotationally restricted isomers.

A compound of the invention, as described above, can be used in the manufacture of a medicament for the prophylactic or therapeutic treatment of a TGF-related disease state in a mammal (animal or human).

A compound of the invention is a potent inhibitor of transforming growth factor ("TGF")-β signaling pathway and are therefore of use in therapy. Accordingly, the present invention provides a method of preventing or treating a TGF-related disease in a mammal (animal or human) comprising the step of administering a therapeutically effective amount of at least one compound of the invention to the animal or human suffering from the TGF-related disease state.

As used herein, the term "therapeutically effective amount" refers to an amount of a compound of the invention required to inhibit the TGF-β signaling pathway. As would be understood by one of skill in the art, a "therapeutically effective amount" will vary from patient to patient and will be determined on a case by case basis. Factors to consider include, but are not limited to, the patient being treated, weight, health, compound administered, etc.

There are numerous disease states that can be treated by inhibition of the TGF-β signaling pathway. Such disease states include, but are not limited to, all types of cancer (e.g., breast, lung, colon, prostate, ovarian, pancreatic, melanoma, all hematological malignancies, etc.) as well as all types of fibrotic diseases (e.g., glomerulonephritis, diabetic nephropathy, hepatic fibrosis, pulmonary fibrosis, arterial hyperplasia and restenosis, scleroderma, and dermal scarring).

The present invention also provides a pharmaceutical composition comprising at least one compound of the invention and at least one pharmaceutically acceptable carrier.

The pharmaceutically acceptable carrier may be any such carrier known in the art including those described in, for example, Remington's Pharmaceutical Sciences, Mack Publishing Co., (A. R. Gennaro edit. 1985). A pharmaceutical composition of the invention may be prepared by conventional means known in the art including, for example, mixing at least one compound of the invention with a pharmaceutically acceptable carrier.

A pharmaceutical composition of the invention may be used in the prevention or treatment of a TGF-related disease state, as described above, in a mammal (animal or human). Thus, a compound of the invention may be formulated as a pharmaceutical composition for oral, buccal, intranasal, parenteral (e.g., intravenous, intramuscular or subcutaneous), topical or rectal administration or in a form suitable for administration by inhalation or insufflation.

For oral administration, the pharmaceutical composition may take the form of, for example, a tablet or capsule prepared by conventional means with a pharmaceutically acceptable excipient such as a binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g., potato starch or sodium starch glycolate); or wetting agent (e.g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional means with a pharmaceutically acceptable additive such as a suspending agent (e.g., sorbitol syrup, methyl cellulose or hydrogenated edible fats); emulsifying agent (e.g., lecithin or acacia); non-aqueous vehicle (e.g., almond oil, oily esters or ethyl alcohol); and preservative (e.g., methyl or propyl p-hydroxybenzoates or sorbic acid).

For buccal administration, the composition may take the form of tablets or lozenges formulated in conventional manner.

A compound of the present invention may also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

A compound of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent. Alternatively, the active ingredient may be in powder form for reconstitution with a suitable vehicle, e.g., sterile pyrogen-free water, before use.

A compound of the invention may also be formulated in rectal compositions such as suppositories or retention enemas, e.g., containing conventional suppository bases such as cocoa butter or other glycerides.

For intranasal administration or administration by inhalation, a compound of the invention may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the compound of the invention. Capsules and cartridges (made, for example, from gelatin) for use in an inhaler or insufflator may be formulated containing a powder mix of a compound of the invention and a suitable powder base such as lactose or starch.

A proposed dose of a compound of the invention for oral, parenteral or buccal administration to the average adult human for the treatment of a TGF-related disease state is about 0.1 mg to about 2000 mg, preferably, about 0.1 mg to about 200 mg of the active ingredient per unit dose which could be administered, for example, 1 to 4 times per day.

Aerosol formulations for treatment of the conditions referred to above in the average adult human are preferably arranged so that each metered dose or "puff" of aerosol contains about 20 μg to about 10,000 μg, preferably, about 20 μg to about 1000 μg of a compound of the invention. The overall daily dose with an aerosol will be within the range about 100 μg to about 100 mg, preferably, about 100 μg to about 10 mg. Administration may be several times daily, for example 2, 3, 4 or 8 times, giving for example, 1, 2 or 3 doses each time.

Aerosol combination formulations for treatment of the conditions referred to above in the average adult human are preferably arranged so that each metered dose or "puff" of aerosol contains from about 0.01 mg to about 1000 mg, preferably, about 0.01 mg to about 100 mg of a compound of this invention, more preferably from about 1 mg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 20,000 mg, preferably, about 0.01 mg to about 2000 mg of a compound of the invention, more preferably from about 1 mg to about 200 mg. Administration may be several times daily, for example 2, 3, 4 or 8 times, giving for example, 1, 2 or 3 doses each time.

For topical administration, a compound of the invention may be formulated as an ointment or cream.

This invention also encompasses pharmaceutical compositions containing and methods of treatment or prevention comprising administering prodrugs of at least one compound of the invention. As used herein, the term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable hydroxyalkyl, or amides prepared by reaction of the parent acid compound with an amine, or basic groups reacted to form an acylated base derivative. Moreover, the prodrug derivatives of this invention may be combined with other features herein taught to enhance bioavailability. For example, a compound of the invention having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain.

According to the invention, in the treatment of a TGF-related disease state, a compound of the invention, as described herein, whether alone or as part of a pharmaceutical composition may be combined with another compound(s) of the invention and/or with another therapeutic agent(s). Examples of suitable therapeutic agent(s) include, but are not limited to, standard non-steroidal anti-inflammatory agents (hereinafter NSAID's) (e.g, piroxicam, diclofenac), propionic acids (e.g., naproxen, flubiprofen, fenoprofen, ketoprofen and ibuprofen), fenamates (e.g., mefenamic acid, indomethacin, sulindac, apazone), pyrazolones (e.g., phenylbutazone), salicylates (e.g., aspirin), COX-2 inhibitors (e.g., celecoxib, valdecoxib, rofecoxib and etoricoxib), analgesics and intraarticular therapies (e.g., corticosteroids) and hyaluronic acids (e.g., hyalgan and synvisc), anticancer agents (e.g., endostatin and angiostatin), cytotoxic drugs (e.g., adriamycin, daunomycin, cis-platinum, etoposide, taxol, taxotere), alkaloids (e.g., vincristine), and antimetabolites (e.g., methotrexate), cardiovascular agents (e.g., calcium channel blockers), lipid lowering agents (e.g., statins), fibrates, beta-blockers, Ace inhibitors, Angiotensin-2 receptor antagonists and platelet aggregation inhibitors, CNS agents (e.g., as antidepressants (such as sertraline)), anti-Parkinsonian drugs (e.g., deprenyl, L-dopa, Requip, Mirapex), MAOB inhibitors (e.g., selegine and rasagiline), comP inhibitors (e.g., Tasmar), A-2 inhibitors, dopamine reuptake inhibitors, NMDA antagonists, Nicotine agonists, Dopamine agonists and inhibitors of neuronal nitric oxide synthase), anti-Alzheimer's drugs (e.g., donepezil, tacrine, COX-2 inhibitors, propentofylline or metryfonate), osteoporosis agents (e.g., roloxifene, droloxifene, lasofoxifene or fosomax), and immunosuppressant agents (e.g., FK-506 and rapamycin).

The following Examples illustrate the preparation of the compounds of the present invention. Melting points are uncorrected. NMR data are reported in parts per million (d) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatograph. The following solvents and gradients were used for the analysis. Solvent A; 98% water/2% acetonirile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 AMU to 1100 AMU. Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

One of ordinary skill in the art will appreciate that in some cases protecting groups may be required during preparation. After the target molecule is made, the protecting group can be removed by methods well known to those of ordinary skill in the art, such as described in Greene and Wuts, "Protective Groups in Organic Synthesis" ($2^{nd}$ Ed, John Wiley & Sons 1991).

Biological Activity

The activity of the compounds of the invention for the various TGF-related disease states described herein can be determined according to one or more of the following assays. According to the invention, a compound of the invention exhibits an in vitro $IC_{50}$ value of about 0.0001 µM–10 µM. By way of illustration, the compound of example 35, as set forth below, exhibits an $IC_{50}$ of 1.19 µM.

The compounds of the present invention also possess differential activity (i.e. are selective for) for TβRII over TβRI and TβRIII. Selectivity is measured in standard assays as a $IC_{50}$ ratio of inhibition in each assay.

TGF-β Type II Receptor (TβRII) Kinase Assay Protocol

Phosphorylation of myelin basic protein (MBP) by the TβRII kinase was measured as follows: 80 microliters of MBP (Upstate Biotechnology #13–104) diluted in kinase reaction buffer (KRB) containing 50 mM MOPS, 5 mM $MgCl_2$, pH 7.2 to yield a final concentration of 3 micromolar MBP was added to each well of a Millipore 96-well multiscreen-DP 0.65 micron filtration plate (#MADPNOB50). 20 microliters of inhibitor diluted in KRB was added to appropriate wells to yield the desired final concentration (10–0.03 micromolar). 10 microliters of a mixture of ATP (Sigma #A-5394) and $^{33}$P-ATP (Perkin Elmer #NEG/602H) diluted in KRB was added to yield a final concentration of 0.25 micromolar ATP and 0.02 microcuries of $^{33}$P-ATP per well. 10 micro liters of a GST-TβRII fusion protein (glutathione S-transferase at the N-terminal end of the cytoplasmic domain of TβRII-amino acids 193–567 with A to V change at 438) diluted in KRB was added to each well to yield a final concentration of 27 nanomolar GST-TβRII. Plates were mixed and incubated for 90 minutes at room temperature.

After the reaction incubation, 100 microliters of cold 20% trichloroacetic acid (Aldrich #25,139–9) was added per well and plates were mixed and incubated for 60 minutes at 4° C. Liquid was then removed from the wells using a Millipore vacuum manifold. Plates were washed once with 200 microliters per well of cold 10% trichloroacetic acid followed by two washes with 100 microliters per well of cold 10% trichloroacetic acid. Plates were allowed to dry overnight at room temperature. 20 microliters of Wallac OptiPhase SuperMix scintillation cocktail was added to each well. Plates were sealed and counted using a Wallac 1450 Microbeta liquid scintillation counter. The potency of inhibitors was determined by their ability to reduce TβRII-mediated phosphorylation of the MBP substrate.

ALK-5 (TβRI) Kinase Assay Protocol

The kinase assays were performed with 65 nM GST-ALK5 and 84 nM GST-Smad3 in 50 mM HEPES, 5 mM $MgCl_2$, 1 mM $CaCl_2$, 1 mM dithiothreitol, and 3_M ATP. Reactions were incubated with 0.5_Ci of [33 P]_ATPfor 3 h at 30° C. Phosphorylated protein was captured on P-81 paper (Whatman, Maidstone, England), washed with 0.5% phosphoric acid, and counted by liquid scintillation. Alternatively, Smad3 or Smad1 protein was also coated onto FlashPlate Sterile Basic Microplates (PerkinElmer Life Sciences, Boston, Mass.). Kinase assays were then performed in Flash-Plates with same assay conditions using either the kinase domain of ALK5 with Smad3 as substrate or the kinase domain of ALK6 (BMP receptor) with Smad1 as substrate. Plates were washed three times with phosphate buffer and counted by TopCount (Packard Bio-science, Meriden, Conn.). (Laping, N.J. et al. *Molecular Pharmacology* 62:58–64 (2002)).

EXAMPLES

Example 1

Step A. Boronic Acid Coupling

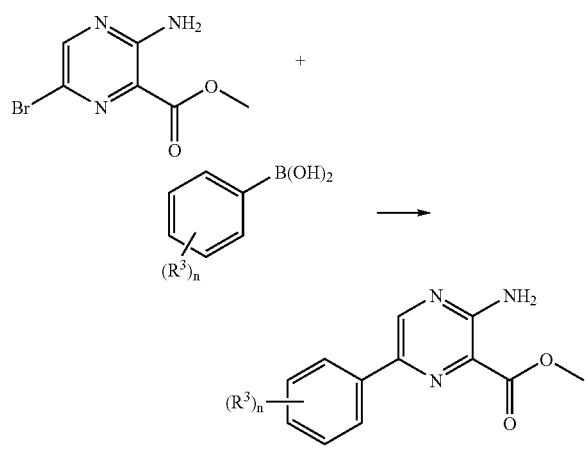

0.15 eq. palladium (II) acetate and 0.2 eq. 1,1'-bis(diphenylphosphino)-ferrocene were combined in dimethylformamide under nitrogen and heated to 50° C. for 20 minutes. $R^3$ and n are each as defined herein. The reaction was allowed to cool to room temperature and 1.0 eq. of the pyrazine, 1.5 eq. of the boronic acid and 1.15 eq. of triethylamine were added. The reaction was heated to 90° for 12 hours and allowed to cool to room temperature. The DMF was removed by rotary evaporation. The crude reaction mixture was dissolved in chloroform and washed twice with 1N aq. HCl and then twice with saturated aq. $NaHCO_3$ solution. The organic layer was dried over sodium sulfate, filtered and concentrated. Material was purified by silica gel chromatography using 100% chloroform as eluent.

Step B. Hydrolysis to Acid

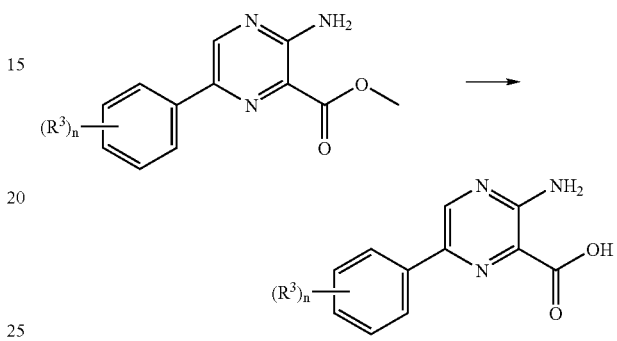

The pyrazine ester (1.0 eq) of Step A was suspended in ethanol and (aq) 3M sodium hydroxide (2.01 eq). The resulting solution was refluxed for 90 minutes. The reaction mixture was allowed to cool to room temperature and 2.01 eq of aq. 3M hydrochloric acid (2.01 eq) was added. After stirring for 60 minutes, the reaction mixture was concentrated to dryness. The acid was used without further purification in Step C below.

Step C. Amide Formation

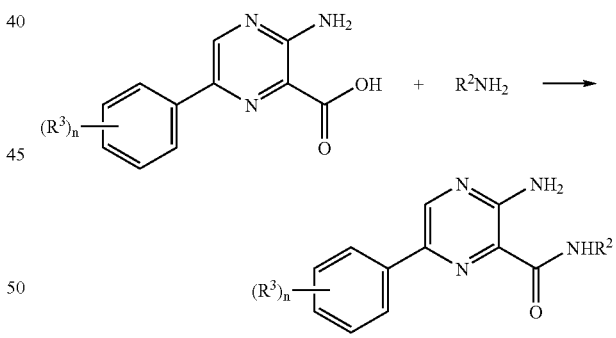

1.0 eq of a 0.2M solution of the acid of Step B in N,N-dimethylacetamide with 3.75% triethylamine was combined with 1.0 eq of a 0.2M solution of the amine $R^2NH_2$ in N,N-dimethylacetamide with 3.75% N-methylmorpholine and 1.5 eq of 0.3M 2-(1H-benzotriazole-1-yl)-1,1,3,3-tetramethyluronium tetrafluoroborate in N,N-dimethylacetamide. $R^2$, $R^3$ and n are each as defined herein. The resulting solution was shaken at 60° C. for 6 hours, and then at room temperature overnight. The reaction mixture was quenched with aq. 10% sodium hydroxide and extracted twice with ethyl acetate. The organic layers dried over sodium sulfate, filtered, and concentrated. Crude reaction mixtures were purified by preparative HPLC.

Example 2

Step A. Boronic Acid Coupling

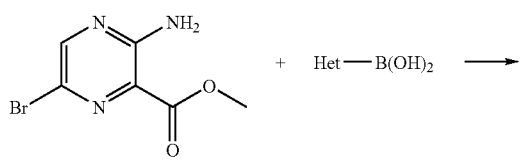

0.15 eq. palladium (II) acetate and 0.2 eq. 1,1'-bis(diphenylphosphino)-ferrocene were combined in dimethylformamide under nitrogen and heated to 50° C. for 20 minutes. Het is as defined herein. The reaction was allowed to cool to room temperature and 1.0 eq. of the pyrazine, 1.5 eq. of the boronic acid and 1.15 eq. of triethylamine were added. The reaction was heated to 90° for 12 hours and allowed to cool to room temperature. The DMF was removed by rotary evaporation. The crude reaction mixture was dissolved in chloroform and washed twice with 1N aq. HCl and then twice with saturated aq. NaHCO$_3$ solution. The organic layer was dried over sodium sulfate, filtered and concentrated. Material was purified by silica gel chromatography using 100% chloroform as eluent.

Step B. Hydrolysis to Acid

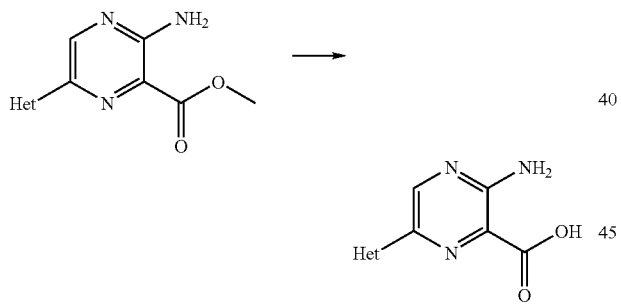

The pyrazine ester (1.0 eq) of Step A was suspended in ethanol and (aq) 3M sodium hydroxide (2.01 eq). Het is as defined herein. The resulting solution was refluxed for 90 minutes. The reaction mixture was allowed to cool to room temperature and 2.01 eq of aq. 3M hydrochloric acid (2.01 eq) was added. After stirring for 60 minutes, the reaction mixture was concentrated to dryness. The acid was used without further purification in Step C below.

Step C. Amide Formation

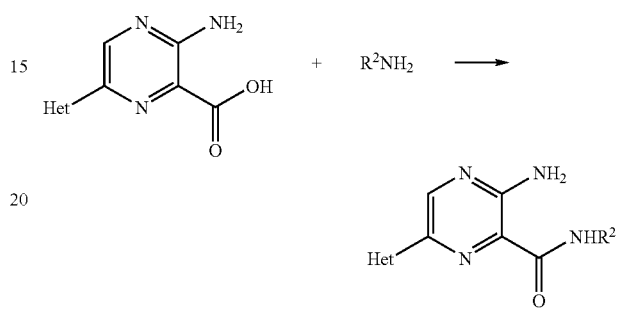

1.0 eq of a 0.2M solution of the acid of Step B in N,N-dimethylacetamide with 3.75% triethylamine was combined with 1.0 eq of a 0.2M solution of the amine R$^2$NH$_2$ in N,N-dimethylacetamide with 3.75% N-methylmorpholine and 1.5 eq of 0.3M 2-(1H-benzotriazole-1-yl)-1,1,3,3-tetramethyluronium tetrafluoroborate in N,N-dimethylacetamide. R$^2$ and Het are each as defined herein. The resulting solution was shaken at 60° C. for 6 hours, and then at room temperature overnight. The reaction mixture was quenched with aq. 10% sodium hydroxide and extracted twice with ethyl acetate. The organic layers dried over sodium sulfate, filtered, and concentrated. Crude reaction mixtures were purified by preparative HPLC.

Examples 3–176

Examples of a compound of formula (I), as described above, are set forth in the Table 1 below. Each of the compounds may be prepared following the procedure set forth in Example 1.

TABLE 1

(I)

| Example | R$^1$ | R$^2$ | R$^3$ where n = 1 |
|---|---|---|---|
| 3 | H | —CH$_2$Ph | H |

LC-MS (M+) = 305;
HPLC (Tr (min)) = 6.16

TABLE 1-continued $$\underset{(R^3)_n}{\text{structure}} \quad (I)$$

Structure: pyrazine with 3-amino, 2-C(O)NR¹R², and 6-(phenyl substituted with (R³)ₙ)

| Example | R¹ | R² | R³ where n = 1 |
|---|---|---|---|
| 4<br>LC-MS (M+) = 285;<br>HPLC (Tr (min)) = 7.77 | H | n-butyl | 4-methyl |
| 5<br>LC-MS (M+) = 305;<br>HPLC (Tr (min)) = 7.94 | H | n-butyl | 4-chloro |
| 6<br>LC-MS (M+) = 283;<br>HPLC (Tr (min)) = 6.65 | R¹ and R² taken together with the nitrogen to which they are attached: pyrrolidine | | 4-methyl |
| 7<br>LC-MS (M+) = 303;<br>HPLC (Tr (min)) = 6.91 | R¹ and R² taken together with the nitrogen to which they are attached: pyrrolidine | | 4-chloro |
| 8<br>LC-MS (M+) = 297;<br>HPLC (Tr (min)) = 6.79 | H | cyclohexyl | H |
| 9<br>LC-MS (M+) = 271;<br>HPLC (Tr (min)) = 6.19 | H | n-butyl | H |
| 10<br>LC-MS (M+) = 283;<br>HPLC (Tr (min)) = 5.65 | H | cyclopentyl | H |
| 11<br>LC-MS (M+) = 311;<br>HPLC (Tr (min)) = 7.2 | H | cycloheptyl | H |
| 12<br>LC-MS (M+) = 291;<br>HPLC (Tr (min)) = 6.57 | H | phenyl | H |
| 13<br>LC-MS (M+) = 269;<br>HPLC (Tr (min)) = 5 | R¹ and R² taken together with the nitrogen to which they are attached: pyrrolidine | | H |
| 14<br>LC-MS (M+) = 331;<br>HPLC (Tr (min)) = 6.77 | H | indan-1-yl | H |
| 15<br>LC-MS (M+) = 300;<br>HPLC (Tr (min)) = 3.47 | H | —(CH₂)₃—N(CH₃)₂ | H |
| 16<br>LC-MS (M+) = 328;<br>HPLC (Tr (min)) = 3.91 | H | —(CH₂)C(CH₃)₂—CH₂N(CH₃)₂ | H |
| 17<br>LC-MS (M+) = 339;<br>HPLC (Tr (min)) = 6.78 | H | benzyl | 4-chloro |

TABLE 1-continued $$\text{(I)}$$

Structure: pyrazine with 3-NH2, 2-C(=O)NR¹R², and 6-(phenyl substituted with (R³)n)

| Example | R¹ | R² | R³ where n = 1 |
|---|---|---|---|
| 18<br>LC-MS (M+) = 317;<br>HPLC (Tr (min)) = 6.98 | H | cyclopentyl | 4-chloro |
| 19<br>LC-MS (M+) = 345;<br>HPLC (Tr (min)) = 7.83 | H | cycloheptyl | 4-chloro |
| 20<br>LC-MS (M+) = 331;<br>HPLC (Tr (min)) = 7.42 | H | cyclohexyl | 4-chloro |
| 21<br>LC-MS (M+) = 305;<br>HPLC (Tr (min)) = 6.8 | H | n-butyl | 3-chloro |
| 22<br>LC-MS (M+) = 317;<br>HPLC (Tr (min)) = 6.94 | H | cyclopentyl | 3-chloro |
| 23<br>LC-MS (M+) = 345;<br>HPLC (Tr (min)) = 7.8 | H | cycloheptyl | 3-chloro |
| 24<br>LC-MS (M+) = 331;<br>HPLC (Tr (min)) = 7.39 | H | cyclohexyl | 3-chloro |
| 25<br>LC-MS (M+) = 303;<br>HPLC (Tr (min)) = 5.74 | R¹ and R² taken together with the nitrogen to which they are attached: pyrrolidine | | 3-chloro |
| 26<br>LC-MS (M+) = 339;<br>HPLC (Tr (min)) = 6.55 | H | benzyl | 2-chloro |
| 27<br>LC-MS (M+) = 305;<br>HPLC (Tr (min)) = 6.55 | H | n-butyl | 2-chloro |
| 28<br>LC-MS (M+) = 317;<br>HPLC (Tr (min)) = 6.67 | H | cyclopentyl | 2-chloro |
| 29<br>LC-MS (M+) = 345;<br>HPLC (Tr (min)) = 7.55 | H | cycloheptyl | 2-chloro |
| 30<br>LC-MS (M+) = 331;<br>HPLC (Tr (min)) = 7.14 | H | cyclohexyl | 2-chloro |
| 31<br>LC-MS (M+) = 303;<br>HPLC (Tr (min)) = 5.26 | R¹ and R² taken together with the nitrogen to which they are attached: pyrrolidine | | 2-chloro |
| 32<br>LC-MS (M+) = 319;<br>HPLC (Tr (min)) = 6.62 | H | benzyl | 4-methyl |
| 33<br>LC-MS (M+) = 297;<br>HPLC (Tr (min)) = 6.78 | H | cyclopentyl | 4-methyl |
| 34<br>LC-MS (M+) = 325;<br>HPLC (Tr (min)) = 7.66 | H | cycloheptyl | 4-methyl |

TABLE 1-continued

Structure (I): 3-amino-6-(phenyl substituted with $(R^3)_n$)-pyrazine-2-carboxamide $NR^1R^2$

| Example | R$^1$ | R$^2$ | R$^3$ where n = 1 |
|---|---|---|---|
| 35<br>LC-MS (M+) = 311;<br>HPLC (Tr (min)) = 7.24 | H | cyclohexyl | 4-methyl |
| 36<br>LC-MS (M+) = 335;<br>HPLC (Tr (min)) = 6.17 | H | benzyl | 4-methoxy |
| 37<br>LC-MS (M+) = 301;<br>HPLC (Tr (min)) = 6.13 | H | n-butyl | 4-methoxy |
| 38<br>LC-MS (M+) = 313;<br>HPLC (Tr (min)) = 6.25 | H | cyclopentyl | 4-methoxy |
| 39<br>LC-MS (M+) = 341;<br>HPLC (Tr (min)) = 7.1 | H | cycloheptyl | 4-methoxy |
| 40<br>LC-MS (M+) = 327;<br>HPLC (Tr (min)) = 6.7 | H | cyclohexyl | 4-methoxy |
| 41<br>LC-MS (M+) = 321;<br>HPLC (Tr (min)) = 6.54 | H | phenyl | 4-methoxy |
| 42<br>LC-MS (M+) = 299;<br>HPLC (Tr (min)) = 4.99 | R$^1$ and R$^2$ taken together with the nitrogen to which they are attached: pyrrolidin-1-yl | | 4-methoxy |
| 43<br>LC-MS (M+) = 349;<br>HPLC (Tr (min)) = 6.48 | H | —CH(CH$_3$)Ph | 4-methoxy |
| 44<br>LC-MS (M+) = 361;<br>HPLC (Tr (min)) = 6.70 | H | indan-1-yl | 4-methoxy |
| 45<br>LC-MS (M+) = 356 | H | 2-oxoazepan-3-yl | 4-methoxy |
| 46<br>LC-MS (M+) = 336;<br>HPLC (Tr (min)) = 4.97 | H | —CH$_2$-2-pyridyl | 4-methoxy |
| 47<br>LC-MS (M+) = 330;<br>HPLC (Tr (min)) = 4.01 | H | —(CH$_2$)$_2$—NHC(=O)CH$_3$ | 4-methoxy |

TABLE 1-continued (I)

| Example | R¹ | R² | R³ where n = 1 |
|---|---|---|---|
| 48<br>LC-MS (M+) = 377;<br>HPLC (Tr (min)) = 7.06 | H | —(CH₂)₄Ph | 4-methoxy |
| 49<br>LC-MS (M+) = 404;<br>HPLC (Tr (min)) = 4.49 | H | benzyl-pyrrolidin-3-yl | 4-methoxy |
| 50<br>LC-MS (M+) = 350<br>HPLC (Tr (min)) = 5.01 | H | —(CH₂)₂-2-pyridyl | 4-methoxy |
| 51<br>LC-MS (M+) = 447<br>HPLC (Tr (min)) = 4.51 | H | 4-benzylpiperazin-1-yl-propyl | 4-methoxy |
| 52<br>LC-MS (M+) = 358;<br>HPLC (Tr (min)) = 3.95 | H | —CH₂C(CH₃)₂CH₂N(CH₃)₂ | 4-methoxy |
| 53<br>LC-MS (M+) = 357 | H | (hydroxymethyl)cyclohexyl | 4-methoxy |
| 54<br>LC-MS (M+) = 379<br>HPLC (Tr (min)) = 5.48 | H | benzyl-hydroxypropyl | 4-methoxy |

TABLE 1-continued (I)

| Example | R¹ | R² | R³ where n = 1 |
|---|---|---|---|
| 55<br>LC-MS (M+) = 441<br>HPLC (Tr (min)) = 6.33 | H | (1,2-diphenyl-2-hydroxyethyl group) | 4-methoxy |
| 56<br>LC-MS (M+) = 377;<br>HPLC (Tr (min)) = 5.61 | H | (trans-2-hydroxy-indan-1-yl) | 4-methoxy |
| 57<br>LC-MS (M+) = 365<br>HPLC (Tr (min)) = 5.31 | H | (2-phenyl-2-hydroxymethyl ethyl) | 4-methoxy |
| 58<br>LC-MS (M−) = 317;<br>HPLC (Tr (min)) = 3.65 | H | —CH(CH$_2$OH)$_2$ | 4-methoxy |
| 59<br>LC-MS (M+) = 289<br>HPLC (Tr (min)) = 3.97 | H | —(CH$_2$)$_2$OH | 4-methoxy |
| 60<br>LC-MS (M+) = 357;<br>HPLC (Tr (min)) = 5.53 | H | (1-hydroxycyclohexyl)methyl | 4-methoxy |
| 61<br>LC-MS (M+) = 331;<br>HPLC (Tr (min)) = 5.09 | H | —CH$_2$C(CH$_3$)$_2$CH$_2$OH | 4-methoxy |
| 62<br>LC-MS (M+) = 372;<br>HPLC (Tr (min)) = 3.62 | H | (2-morpholinoethyl) | 4-methoxy |
| 63<br>LC-MS (M+) = 326 | H | (2-oxoazepan-3-yl) | H |
| 64<br>LC-MS (M+) = 306;<br>HPLC (Tr (min)) = 4.95 | H | —CH$_2$-2-pyridyl | H |

TABLE 1-continued (I)

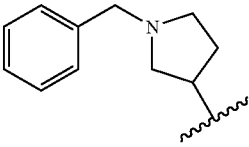

| Example | R¹ | R² | R³ where n = 1 |
|---|---|---|---|
| 65<br>LC-MS (M+) = 300;<br>HPLC (Tr (min)) = 3.94 | H | —(CH₂)₂—NHC(=O)CH₃ | H |
| 66<br>LC-MS (M+) = 273<br>HPLC (Tr (min)) = 4.75 | H | —(CH₂)₂—OCH₃ | H |
| 67<br>LC-MS (M+) = 347;<br>HPLC (Tr (min)) = 7.15 | H | —(CH₂)₄Ph | H |
| 68<br>LC-MS (M+) = 374<br>HPLC (Tr (min)) = 4.43 | H | 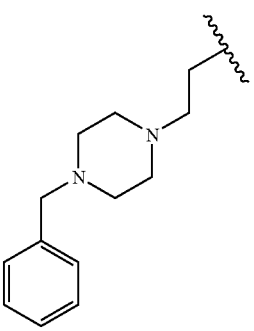 | H |
| 69<br>LC-MS (M+) = 320<br>HPLC (Tr (min)) = 4.99 | H | —(CH₂)₂-2-pyridyl | H |
| 70<br>LC-MS (M+) = 417<br>HPLC (Tr (min)) = 4.45 | H | 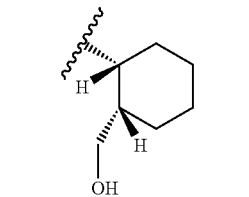 | H |
| 71<br>LC-MS (M+) = 327<br>HPLC (Tr (min)) = 5.61 | H | 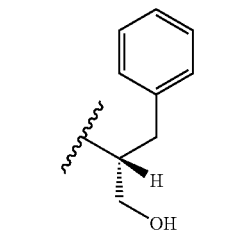 | H |
| 72<br>LC-MS (M+) = 343/325;<br>HPLC (Tr (min)) = 5.55 | H | —CH(CH₃)(CH₂)₃C(CH₃)₂OH | H |
| 73<br>LC-MS (M+) = 349<br>HPLC (Tr (min)) = 5.49 | H |  | H |

TABLE 1-continued
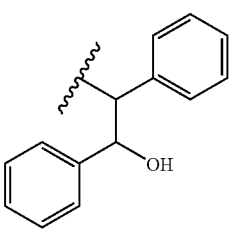
(I)
| Example | R¹ | R² | R³ where n = 1 |
|---|---|---|---|
| 74<br>LC-MS (M+) = 411;<br>HPLC (Tr (min)) = 6.38 | H | 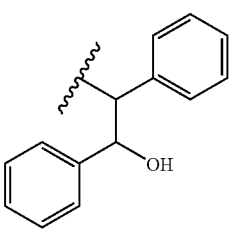 | H |
| 75<br>LC-MS (M+) = 347;<br>HPLC (Tr (min)) = 5.60 | H | 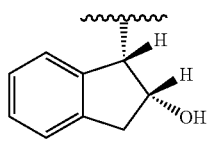 | H |
| 76<br>LC-MS (M+) = 335<br>HPLC (Tr (min)) = 5.31 | H | 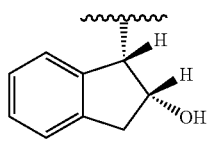 | H |
| 77<br>LC-MS (M+) = 289;<br>HPLC (Tr (min)) = 3.55 | H | —CH(CH$_2$OH)$_2$ | H |
| 78<br>LC-MS (M+) = 259<br>HPLC (Tr (min)) = 3.88 | H | —(CH$_2$)$_2$OH | H |
| 79<br>LC-MS (M+) = 327;<br>HPLC (Tr (min)) = 5.53 | H | 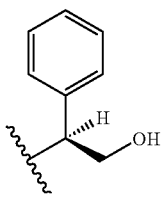 | H |
| 80<br>LC-MS (M+) = 301;<br>HPLC (Tr (min)) = 5.07 | H | —CH$_2$C(CH$_3$)$_2$CH$_2$OH | H |
| 81<br>LC-MS (M+) = 327<br>HPLC (Tr (min)) = 4.6 | H | 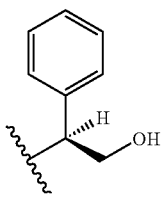 | 4-methyl |

TABLE 1-continued (I)

Structure: pyrazine with NH2, NR¹R² carboxamide, and (R³)n-phenyl substituent

| Example | R¹ | R² | R³ where n = 1 |
|---|---|---|---|
| 82<br>LC-MS (M+) = 427 | H | (S)-2-benzyl-3-hydroxypropyl group (CH2Ph, CH2OH on stereocenter) | 4-SO2CH3 |
| 83<br>LC-MS (M+) = 489 | H | 1,2-diphenyl-2-hydroxyethyl-CH group | 4-SO2CH3 |
| 84<br>LC-MS (M+) = 361 | H | trans-2-hydroxyindan-1-yl | 4-methyl |
| 85<br>LC-MS (M+) = 349 | H | 2-phenyl-3-hydroxypropyl (stereodefined) | 4-methyl |
| 86<br>LC-MS (M+) = 413 | H | 2-phenyl-3-hydroxypropyl (stereodefined) | 4-SO2CH3 |
| 87<br>LC-MS (M+) = 303 | H | —CH(CH2OH)2 | 4-methyl |
| 88<br>LC-MS (M+) = 367 | H | —CH(CH2OH)2 | 4-SO2CH3 |
| 89<br>LC-MS (M+) = 273<br>HPLC (Tr (min)) = 4.36 | H | —(CH2)2OH | 4-methyl |
| 90<br>LC-MS (M+) = 315<br>HPLC (Tr (min)) = 5.52 | H | —CH2C(CH3)2CH2OH | 4-methyl |
| 91<br>LC-MS (M+) = 379<br>HPLC (Tr (min)) = 4.30 | H | —CH2C(CH3)2CH2OH | 4-SO2CH3 |

TABLE 1-continued (I)

Structure: pyrazine with 3-NH₂, 2-C(O)NR¹R², 6-(R³)ₙ-phenyl

| Example | R¹ | R² | R³ where n = 1 |
|---|---|---|---|
| 92 LC-MS (M+) = 383 | H | (S)-1-hydroxy-3-phenylpropan-2-yl (CH₂Ph, CH₃, CH₂OH with H on stereocenter) | 4-chloro |
| 93 LC-MS (M+) = 383 | H | (S)-1-hydroxy-3-phenylpropan-2-yl | 3-chloro |
| 94 LC-MS (M+) = 383 | H | (S)-1-hydroxy-3-phenylpropan-2-yl | 2-chloro |
| 95 LC-MS (M+) = 381 | H | cis-2-hydroxy-2,3-dihydro-1H-inden-1-yl (mixture at attachment) | 4-chloro |
| 96 LC-MS (M+) = 381 | H | cis-2-hydroxy-2,3-dihydro-1H-inden-1-yl | 3-chloro |
| 97 LC-MS (M+) = 381 | H | cis-2-hydroxy-2,3-dihydro-1H-inden-1-yl | 2-chloro |
| 98 LC-MS (M+) = 369 | H | (S)-2-hydroxy-1-phenylethyl | 4-chloro |

TABLE 1-continued

Structure (I): 3-amino-pyrazine with C(=O)NR¹R² at one position and (R³)ₙ-phenyl at another position.

| Example | R¹ | R² | R³ where n = 1 |
|---|---|---|---|
| 99<br>LC-MS (M+) = 369 | H | (S)-2-phenyl-2-hydroxymethyl-ethyl (CHPh-CH₂OH) | 3-chloro |
| 100<br>LC-MS (M+) = 369 | H | (R)-2-phenyl-2-hydroxymethyl-ethyl (CHPh-CH₂OH) | 2-chloro |
| 101<br>LC-MS (M+) = 323 | H | —CH(CH₂OH)₂ | 4-chloro |
| 102<br>LC-MS (M+) = 323 | H | —CH(CH₂OH)₂ | 3-chloro |
| 103<br>LC-MS (M+) = 323 | H | —CH(CH₂OH)₂ | 2-chloro |
| 104<br>LC-MS (M+) = 293 | H | —(CH₂)₂OH | 4-chloro |
| 105<br>LC-MS (M+) = 293<br>HPLC (Tr (min)) = 4.50 | H | —(CH₂)₂OH | 3-chloro |
| 106<br>LC-MS (M+) = 293<br>HPLC (Tr (min)) = 4.23 | H | —(CH₂)₂OH | 2-chloro |
| 107<br>LC-MS (M+) = 335<br>HPLC (Tr (min)) = 5.70 | H | —CH₂C(CH₃)₂CH₂OH | 3-chloro |
| 108<br>LC-MS (M+) = 335<br>HPLC (Tr (min)) = 5.39 | H | —CH₂C(CH₃)₂CH₂OH | 2-chloro |
| 109<br>LC-MS (M+) = 334 | H | —(CH₂)₂-2-pyridyl | 4-methyl |
| 110<br>LC-MS (M+) = 398 | H | —(CH₂)₂-2-pyridyl | 4-SO₂CH₃ |
| 111<br>LC-MS (M+) = 354 | H | —(CH₂)₂-2-pyridyl | 4-chloro |
| 112<br>LC-MS (M+) = 354 | H | —(CH₂)₂-2-pyridyl | 3-chloro |
| 113<br>LC-MS (M+) = 354 | H | —(CH₂)₂-2-pyridyl | 2-chloro |
| 114<br>LC-MS (M+) = 334 | H | —(CH₂)₂—NHC(=O)CH₃ | 4-chloro |
| 115<br>LC-MS (M+) = 334 | H | —(CH₂)₂—NHC(=O)CH₃ | 3-chloro |
| 116<br>LC-MS (M+) = 361 | H | cyclopentyl | 4-SO₂CH₃ |
| 117<br>LC-MS (M+) = 340 | H | 3-(2-oxo-azepanyl) | 4-methyl |

TABLE 1-continued (I)

Structure: pyrazine with 3-NH$_2$, 2-C(=O)NR$^1$R$^2$, 6-(phenyl substituted with (R$^3$)$_n$)

| Example | R$^1$ | R$^2$ | R$^3$ where n = 1 |
|---|---|---|---|
| 118 | H | —CH$_2$C(CH$_3$)$_2$CH$_2$OH | H |
| LC-MS (M+) = 301 | | | |
| HPLC (Tr (min)) = 5.06 | | | |
| 119 | H | —CH$_2$C(CH$_3$)$_2$CH$_2$OH | 4-methoxy |
| LC-MS (M+) = 331 | | | |
| HPLC (Tr (min)) = 5.08 | | | |
| 120 | H | —CH$_2$CH(OH)CH$_2$OH | H |
| LC-MS (M+) = 289 | | | |
| HPLC (Tr (min)) = 3.62 | | | |
| 121 | H | —CH$_2$CH(OH)CH$_2$OH | 3-chloro |
| LC-MS (M+) = 323 | | | |
| HPLC (Tr (min)) = 4.19 | | | |
| 122 | H | —CH$_2$CH(OH)CH$_2$OH | 2-chloro |
| LC-MS (M+) = 323 | | | |
| HPLC (Tr (min)) = 3.83 | | | |
| 123 | H | —CH$_2$CH(OH)CH$_2$OH | 4-methoxy |
| LC-MS (M+) = 319 | | | |
| HPLC (Tr (min)) = 3.72 | | | |
| 124 | H | —CH$_2$CH(OH)CH$_2$OH | 4-methyl |
| LC-MS (M+) = 303 | | | |
| HPLC (Tr (min)) = 3.94 | | | |
| 125 | H | —CH$_2$CH(OH)CH$_2$OH | 3-methoxy |
| LC-MS (M+) = 319 | | | |
| HPLC (Tr (min)) = 3.79 | | | |
| 126 | H | —CH$_2$CH(OH)CH$_2$OH | 2-methoxy |
| LC-MS (M+) = 319 | | | |
| HPLC (Tr (min)) = 3.75 | | | |
| 127 | H | —CH$_2$CH(OH)CH$_2$OH | 4-CN |
| LC-MS (M+) = 314 | | | |
| HPLC (Tr (min)) = 3.80 | | | |
| 128 | H | —(CH$_2$)$_3$OH | 3-methoxy |
| LC-MS (M+) = 303 | | | |
| HPLC (Tr (min)) = 4.26 | | | |
| 129 | H | —(CH$_2$)$_3$OH | 2-methoxy |
| LC-MS (M+) = 303 | | | |
| HPLC (Tr (min)) = 4.25 | | | |
| 130 | H | —(CH$_2$)$_3$OH | 4-CN |
| LC-MS (M+) = 298 | | | |
| HPLC (Tr (min)) = 4.06 | | | |
| 131 | H | —(CH$_2$)$_2$OH | 4-C(=O)CH$_3$ |
| LC-MS (M+) = 301 | | | |
| HPLC (Tr (min)) = 3.70 | | | |
| 132 | H | —(CH$_2$)$_2$OH | 3-methoxy |
| LC-MS (M+) = 289 | | | |
| HPLC (Tr (min)) = 4.05 | | | |
| 133 | H | —(CH$_2$)$_2$OH | 2-methoxy |
| LC-MS (M+) = 289 | | | |
| HPLC (Tr (min)) = 4.02 | | | |
| 134 | H | —(CH$_2$)$_2$OH | 4-CN |
| LC-MS (M+) = 284 | | | |
| HPLC (Tr (min)) = 3.80 | | | |
| 135 | H | —CH$_2$C(CH$_3$)$_2$CH$_2$OH | 4-C(=O)CH$_3$ |
| LC-MS (M+) = 343 | | | |
| HPLC (Tr (min)) = 4.75 | | | |
| 136 | H | —CH$_2$C(CH$_3$)$_2$CH$_2$OH | 3-methoxy |
| LC-MS (M+) = 331 | | | |
| HPLC (Tr (min)) = 5.16 | | | |
| 137 | H | —CH$_2$C(CH$_3$)$_2$CH$_2$OH | 2-methoxy |
| LC-MS (M+) = 331 | | | |
| HPLC (Tr (min)) = 5.17 | | | |
| 138 | H | —CH$_2$C(CH$_3$)$_2$CH$_2$OH | 4-CN |
| LC-MS (M+) = 326 | | | |
| HPLC (Tr (min)) = 4.90 | | | |
| 139 | H | —CH$_2$CH(OH)CH$_2$OH | 4-C(=O)CH$_3$ |
| LC-MS (M+) = 331 | | | |
| HPLC (Tr (min)) = 3.50 | | | |

TABLE 1-continued

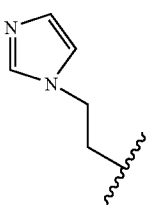

| Example | R$^1$ | R$^2$ | R$^3$ where n = 1 |
|---|---|---|---|
| 140<br>LC-MS (M+) = 358<br>HPLC (Tr (min)) = 4.71 | H | —CH$_2$CH(OH)CH$_2$OH | 2,3-dichloro |
| 141<br>LC-MS (M+) = 307<br>HPLC (Tr (min)) = 4.45 | H | —(CH$_2$)$_3$OH | 2-chloro |
| 142<br>LC-MS (M+) = 303<br>HPLC (Tr (min)) = 4.18 | H | —(CH$_2$)$_3$OH | 4-methoxy |
| 143<br>LC-MS (M+) = 315<br>HPLC (Tr (min)) = 3.95 | H | —(CH$_2$)$_3$OH | 4-C(=O)CH$_3$ |
| 144<br>LC-MS (M+) = 351<br>HPLC (Tr (min)) = 4.90 | H | —(CH$_2$)$_3$OH | 4-bromo |
| 145<br>LC-MS (M+) = 328<br>HPLC (Tr (min)) = 5.06 | H | —(CH$_2$)$_2$OH | 2,3-dichloro |
| 146<br>LC-MS (M+) = 337<br>HPLC (Tr (min)) = 4.68 | H | —(CH$_2$)$_2$OH | 4-bromo |
| 147<br>LC-MS (M+) = 370<br>HPLC (Tr (min)) = 6.24 | H | —CH$_2$C(CH$_3$)$_2$CH$_2$OH | 2,3-dichloro |
| 148<br>LC-MS (M+) = 379<br>HPLC (Tr (min)) = 5.84 | H | —CH$_2$C(CH$_3$)$_2$CH$_2$OH | 4-bromo |
| 149<br>LC-MS (M+) = 303<br>HPLC (Tr (min)) = 4.78 | H | —(CH$_2$)$_2$OCH$_3$ | 4-methoxy |
| 150<br>LC-MS (M+) = 353<br>HPLC (Tr (min)) = 3.75 | H | (imidazolyl-propyl group) | 4-methoxy |
| 151<br>LC-MS (M+) = 289<br>HPLC (Tr (min)) = 3.62 | H | —CH$_2$CH(OH)CH$_2$OH | H |
| 152<br>LC-MS (M+) = 323<br>HPLC (Tr (min)) = 4.19 | H | —CH$_2$CH(OH)CH$_2$OH | 3-chloro |
| 153<br>LC-MS (M+) = 323<br>HPLC (Tr (min)) = 3.83 | H | —CH$_2$CH(OH)CH$_2$OH | 2-chloro |
| 154<br>LC-MS (M+) = 319<br>HPLC (Tr (min)) = 3.72 | H | —CH$_2$CH(OH)CH$_2$OH | 4-methoxy |
| 155<br>LC-MS (M+) = 319<br>HPLC (Tr (min)) = 3.79 | H | —CH$_2$CH(OH)CH$_2$OH | 3-methoxy |
| 156<br>LC-MS (M+) = 319<br>HPLC (Tr (min)) = 3.75 | H | —CH$_2$CH(OH)CH$_2$OH | 2-methoxy |
| 157<br>LC-MS (M+) = 214<br>HPLC (Tr (min)) = 3.80 | H | —CH$_2$CH(OH)CH$_2$OH | 4-CN |

TABLE 1-continued $$\text{(I)}$$

Structure: Pyrazine ring with 3-NH$_2$, 2-C(=O)NR$^1$R$^2$, and 6-(phenyl substituted with (R$^3$)$_n$)

| Example | R$^1$ | R$^2$ | R$^3$ where n = 1 |
|---|---|---|---|
| 158<br>LC-MS (M+) = 303<br>HPLC (Tr (min)) = 4.26 | H | —(CH$_2$)$_3$OH | 3-methoxy |
| 159<br>LC-MS (M+) = 303<br>HPLC (Tr (min)) = 4.25 | H | —(CH$_2$)$_3$OH | 2-methoxy |
| 160<br>LC-MS (M+) = 298<br>HPLC (Tr (min)) = 4.06 | H | —(CH$_2$)$_3$OH | 4-CN |
| 161<br>LC-MS (M+) = 259<br>HPLC (Tr (min)) = 3.88 | H | —(CH$_2$)$_2$OH | H |
| 162<br>LC-MS (M+) = 293<br>HPLC (Tr (min)) = 4.50 | H | —(CH$_2$)$_2$OH | 3-chloro |
| 163<br>LC-MS (M+) = 293<br>HPLC (Tr (min)) = 4.23 | H | —(CH$_2$)$_2$OH | 2-chloro |
| 164<br>LC-MS (M+) = 273<br>HPLC (Tr (min)) = 4.36 | H | —(CH$_2$)$_2$OH | 4-methyl |
| 165<br>LC-MS (M+) = 289<br>HPLC (Tr (min)) = 3.97 | H | —(CH$_2$)$_2$OH | 4-methoxy |
| 166<br>LC-MS (M+) = 301<br>HPLC (Tr (min)) = 3.70 | H | —(CH$_2$)$_2$OH | 4-C(=O)CH$_3$ |
| 167<br>LC-MS (M+) = 289<br>HPLC (Tr (min)) = 4.05 | H | —(CH$_2$)$_2$OH | 3-methoxy |
| 168<br>LC-MS (M+) = 289<br>HPLC (Tr (min)) = 4.02 | H | —(CH$_2$)$_2$OH | 2-methoxy |
| 169<br>LC-MS (M+) = 284<br>HPLC (Tr (min)) = 3.80 | H | —(CH$_2$)$_2$OH | 4-CN |
| 170<br>LC-MS (M+) = 335<br>HPLC (Tr (min)) = 5.70 | H | —CH$_2$C(CH$_3$)$_2$CH$_2$OH | 3-chloro |
| 171<br>LC-MS (M+) = 335<br>HPLC (Tr (min)) = 5.39 | H | —CH$_2$C(CH$_3$)$_2$CH$_2$OH | 2-chloro |
| 172<br>LC-MS (M+) = 379<br>HPLC (Tr (min)) = 4.30 | H | —CH$_2$C(CH$_3$)$_2$CH$_2$OH | 4-SO$_2$CH$_3$ |
| 173<br>LC-MS (M+) = 343<br>HPLC (Tr (min)) = 4.75 | H | —CH$_2$C(CH$_3$)$_2$CH$_2$OH | 4-C(=O)CH$_3$ |
| 174<br>LC-MS (M+) = 331<br>HPLC (Tr (min)) = 5.16 | H | —CH$_2$C(CH$_3$)$_2$CH$_2$OH | 3-methoxy |
| 175<br>LC-MS (M+) = 331<br>HPLC (Tr (min)) = 5.17 | H | —CH$_2$C(CH$_3$)$_2$CH$_2$OH | 2-methoxy |
| 176<br>LC-MS (M+) = 326<br>HPLC (Tr (min)) = 4.90 | H | —CH$_2$C(CH$_3$)$_2$CH$_2$OH | 4-CN |

Examples 177–214

Examples of a compound of formula (II), as described above, are set forth in in Table 2 below. Each of the compounds may be prepared according to the procedure set forth in Example 2.

TABLE 2

(II)

*Structure: pyrazine with 3-amino, 6-Het, 2-C(=O)NR¹R²*

| Compound | R¹ | R² | Het |
|---|---|---|---|
| 177 LC-MS (M+) = 339 | H | (S)-CH(CH₃)CH₂-phenyl with CH₂OH (1-phenyl-2-hydroxypropan-2-yl type, shown as benzyl-CH(CH₃)-CH₂OH) | 2-furanyl |
| 178 LC-MS (M+) = 355 | H | (same type as 177) benzyl-CH(CH₃)-CH₂OH | 3-thienyl |
| 179 LC-MS (M+) = 417 | H | —CH(phenyl)CH(phenyl)OH | 3-thienyl |
| 180 LC-MS (M+) = 353 | H | trans-2-hydroxy-indan-1-yl | 3-thienyl |
| 181 LC-MS (M+) = 325 | H | (R)-2-hydroxy-1-phenylethyl (PhCH(–)CH₂OH) | 2-furanyl |

TABLE 2-continued (II)

*Structure: pyrazine with 3-amino, 6-Het, 2-C(=O)NR¹R²*

| Compound | R¹ | R² | Het |
|---|---|---|---|
| 182 LC-MS (M+) = 341 | H | (R)-2-hydroxy-1-phenylethyl | 3-thienyl |
| 183 LC-MS (M+) = 295 | H | —CH(CH₂OH)₂ | 3-thienyl |
| 184 LC-MS (M+) = 265 HPLC (Tr (min)) = 3.69 | H | —(CH₂)₂OH | 3-thienyl |
| 185 LC-MS (M+) = 307 HPLC (Tr (min)) = 4.88 | H | —CH₂C(CH₃)₂CH₂OH | 3-thienyl |
| 186 LC-MS (M+) = 364 | H | 1-benzylpyrrolidin-3-yl | 2-furanyl |
| 187 LC-MS (M+) = 380 | H | 1-benzylpyrrolidin-3-yl | 3-thienyl |
| 188 LC-MS (M+) = 332 | H | —(CH₂)₃-4-morpholinyl | 2-furanyl |
| 189 LC-MS (M+) = 290 | H | —(CH₂)₃—N(CH₃)₂ | 2-furanyl |
| 190 LC-MS (M+) = 326 | H | —(CH₂)₂-2-pyridyl | 3-thienyl |
| 191 LC-MS (M+) = 301 | \multicolumn{2}{l}{R¹ and R² taken together with the nitrogen to which they are attached: 2,5-dimethyl-2,5-dihydro-1H-pyrrol-1-yl} | 3-thienyl |
| 192 LC-MS (M+) = 312 | H | —CH₂-2-pyridyl | 3-thienyl |
| 193 LC-MS (M+) = 306 | H | —(CH₂)₂—NC(=O)CH₃ | 3-thienyl |
| 194 LC-MS (M+) = 289 | H | cyclopentyl | 3-thienyl |

TABLE 2-continued (II)

| Compound | R¹ | R² | Het |
|---|---|---|---|
| 195 LC-MS (M+) = 325 | H | —CH(CH₃)Ph | 3-thienyl |
| 196 LC-MS (M+) = 337 | H | (indanyl) | 3-thienyl |
| 197 LC-MS (M+) = 332 | H | (azepanone) | 3-thienyl |
| 198 LC-MS (M+) = 337 HPLC (Tr (min)) = 3.7 | H | —CH₂CH(OH)CH₂OH | 2-thienyl-5-acetyl |
| 199 LC-MS (M+) = 329 HPLC (Tr (min)) = 4.20 | H | —CH₂CH(OH)CH₂OH | 2-benzofuranyl |
| 200 LC-MS (M+) = 321 HPLC (Tr (min)) = 3.80 | H | —(CH₂)₃OH | 2-thienyl-5-acetyl |
| 201 LC-MS (M+) = 313 HPLC (Tr (min)) = 4.80 | H | —(CH₂)₃OH | 2-benzofuranyl |
| 202 LC-MS (M+) = 299 HPLC (Tr (min)) = 4.6 | H | —(CH₂)₂OH | 2-benzofuranyl |
| 203 LC-MS (M+) = 349 HPLC (Tr (min)) = 4.7 | H | —CH₂C(CH₃)₂CH₂OH | 2-thienyl-5-acetyl |
| 204 LC-MS (M+) = 279 HPLC (Tr (min)) = 3.93 | H | —(CH₂)₃OH | 3-thienyl |
| 205 LC-MS (M+) = 307 HPLC (Tr (min)) = 3.70 | H | —(CH₂)₂OH | 2-thienyl-5-acetyl |
| 206 LC-MS (M+) = 302 HPLC (Tr (min)) = 3.80 | H | —CH₂C(CH₃)₂CH₂OH | 2-pyridyl |
| 207 LC-MS (M+) = 337 HPLC (Tr (min)) = 3.70 | H | —CH₂CH(OH)CH₂OH | 2-thienyl-5-acetyl |
| 208 LC-MS (M+) = 329 HPLC (Tr (min)) = 4.20 | H | —CH₂CH(OH)CH₂OH | 2-benzofuranyl |
| 209 LC-MS (M+) = 321 HPLC (Tr (min)) = 3.80 | H | —(CH₂)₃OH | 2-thienyl-5-acetyl |
| 210 LC-MS (M+) = 313 HPLC (Tr (min)) = 4.80 | H | —(CH₂)₃OH | 2-benzofuranyl |
| 211 LC-MS (M+) = 299 HPLC (Tr (min)) = 4.60 | H | —(CH₂)₂OH | 2-benzofuranyl |
| 212 LC-MS (M+) = 307 HPLC (Tr (min)) = 4.88 | H | —CH₂C(CH₃)₂CH₂OH | 3-thienyl |
| 213 LC-MS (M+) = 291 HPLC (Tr (min)) = 4.75 | H | —CH₂C(CH₃)₂CH₂OH | 2-furanyl |
| 214 LC-MS (M+) = 349 HPLC (Tr (min)) = 4.70 | H | —CH₂C(CH₃)₂CH₂OH | 2-thienyl-5-acetyl |

Example 215–217

Examples of a compound of formula (III), as described above, are set forth in Table 3. Each of the compounds may be prepared by following the procedure set forth in Example 1.

TABLE 3

(III)

| Compound | R¹ | R² | Ar |
|---|---|---|---|
| 215 LC-MS (M+) = 323 HPLC (Tr(min)) = 4.87 | H | —(CH₂)₃OH | 1-naphthyl |
| 216 LC-MS (M+) = 351 HPLC (Tr(min)) = 5.79 | H | —CH₂C(CH₃)₂CH₂OH | 1-naphthyl |
| 217 LC-MS (M+) = 351 HPLC (Tr(min)) = 5.79 | H | —CH₂C(CH₃)₂CH₂OH | 1-naphthyl |

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The claimed invention is:

1. A compound of formula (I):

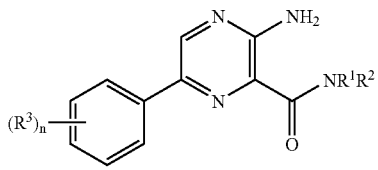

or a pharmaceutically acceptable salt or hydrate thereof where:

$R^1$ is H;

$R^2$ is a substituted or unsubstituted $(C_6-C_8)$alkyl, $(C_3-C_9)$cycloalkyl, $(C_3-C_9)$cycloalkyl$(C_1-C_8)$ alkyl, $(C_3-C_9)$aryl, $(C_3-C_9)$aryl$(C_1-C_8)$alkyl, $(C_3-C_9)$heteroaryl, $(C_3-C_9)$heteroaryl$(C_1-C_8)$ alkyl, $(C_6-C_8)$hydroxyalkyl, $(C_3-C_9)$heterocyclyl, $(C_3-C_9)$heterocyclyl$(C_1-C_8)$alkyl, $(C_1-C_8)$alkyl$(C_3-C_9)$aryl, $(C_1-C_8)$alkylamine, $(C_1-C_8)$alkylamide; or $R^1$ and $R^2$ taken together with the nitrogen to which they are attached form a substituted or unsubstituted $(C_3-C_9)$ heterocyclyl or heteroaryl;

$R^3$ is independently selected from the group consisting of H, $(C_1-C_8$alkyl, halo, $(C_1-C_8)$alkoxy, $(C_1-C_8)$alkyl-$SO_2-$, cyano, and $(C_1-C_8)$alkylC(=O)—;

n is an integer from 0–5;

wherein "substituted" refers to one or more substitutions with a substituent selected from the group consisting of cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, —O—$(C_1-C_6)$alkyl, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl;

with the proviso that the compound is not 3-amino-6-phenyl-pyrazine-2-carboxylic acid butylamide or 3-amino-6-phenyl-pyrazine-2-carboxylic acid (2-hydroxy-ethyl)-amide.

2. A compound of claim 1, wherein $R^3$ is H, bromo, chloro, cyano, methoxy, $(C_1-C_8)$alkyl-$SO_2-$, or $(C_1-C_8)$alkylC(=O)—.

3. A compound of claim 1, wherein n is 0–4.

4. A compound of claim 3, wherein n is 0–1.

5. A compound of formula (II):

or a pharmaceutically acceptable salt or hydrate thereof where:

$R^1$ is H;

$R^2$ is a substituted or unsubstituted $(C_6-C_8)$alkyl, $(C_3-C_9)$cycloalkyl, $(C_3-C_9)$cycloalkyl$(C_1-C_8)$ alkyl, $(C_3-C_9)$aryl, $(C_3-C_9)$aryl$(C_1-C_8)$alkyl, $(C_3-C_9)$heteroaryl, $(C_3-C_9)$heteroaryl$(C_1-C_8)$ alkyl, $(C_1-C_8)$hydroxyalkyl, $(C_3-C_9)$heterocyclyl, $(C_3-C_9)$heterocyclyl$(C_1-C_8)$ alkyl, $(C_1-C_8)$alkyl$(C_3-C_9)$aryl,$(C_1-C_8)$alkylamine, $(C_1-C_8)$alkylamide; or $R^1$ and $R^2$ taken together with the nitrogen to which they are attached form a substituted or unsubstituted $(C_3-C_9)$ heterocyclyl or heteroaryl;

Het is a substituted or unsubstituted heterocyclyl or heteroaryl group containing at least one heteroatom selected from N, O and S;

wherein "substituted" refers to one or more substitutions with a substituent selected from the group consisting of cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, —O—$(C_1-C_6)$alkyl, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl.

6. A compound of claim 5, wherein Het is a substituted or unsubstituted $(C_5-C_{10})$heterocyclyl or heteroaryl group containing at least one heteroatom selected from N, O and S.

7. A compound of claim 6, wherein Het is a substituted or unsubstituted furanyl, thienyl, pyridyl, or benzofuranyl group.

8. A compound of formula (III):

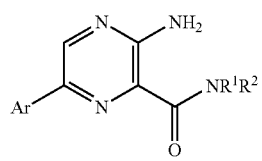

or a pharmaceutically acceptable salt or hydrate thereof where:

$R^1$ is H;

$R^2$ is a substituted or unsubstituted $(C_1-C_8)$hydroxyalkyl;

Ar is a substituted or unsubstituted $(C_3-C_9)$aryl group;

wherein "substituted" refers to one or more substitutions with a substituent selected from the group consisting of cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, —O—$(C_1-C_6)$alkyl, aryl or heteroaryl, aryloxy or heteroaryloxy, aralkyl or heteroaralkyl, aralkoxy or heteroaralkoxy, HO—(C=O)—, ester, amido, ether, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl;

with the proviso that the compound is not 3-amino-6-phenyl-pyrazine-2-carboxylic acid butylamide or 3-amino-6-phenyl-pyrazine-2-carboxylic acid (2-hydroxy-ethyl)-amide.

9. A compound of claim 8, wherein $R^2$ is a substituted or unsubstituted $(C_1-C_5)$alcohol.

10. A compound of claim 9, wherein $R^2$ is a substituted or unsubstituted $(C_3-C_5)$alcohol.

11. A compound of claim 8, wherein Ar is a substituted or unsubstituted naphthyl group.

12. A compound of claim 1 wherein $R^2$ is a substituted or unsubstituted $(C_1-C_8)$alkyl$(C_3-C_9)$ aryl;

$R^3$ is independently selected from the group consisting of H, $(C_1-C_8)$alkyl, halo, $(C_1-C_8)$ alkoxy, $(C_1-C_8)$alkyl-$SO_2$—, cyano, and $(C_1-C_8)$alkylC(=O)—; and n is 0–4;

wherein "substituted" refers to one or more substitutions with a substituent selected from the group consisting of cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, —O—$(C_1-C_6)$alkyl, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl.

13. A compound of claim 12, where $R^3$ is independently selected from the group consisting of H, or bromo, chloro, and methoxy.

14. A compound of claim 13 wherein n=0 and $R^3$ is an unsubstituted $(C_1-C_8)$alkyl$(C_3-C_9)$aryl;

wherein "substituted" refers to one or more substitutions with a substituent selected from the group consisting of cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, —O—$(C_1-C_6)$alkyl, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl.

15. A compound of claim 14 wherein said $(C_1-C_8)$alkyl $(C_3-C_9)$aryl is $CH_2$ phenyl.

16. A compound of formula (I):

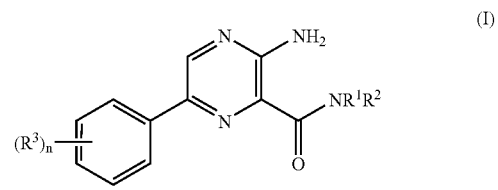

or a pharmaceutically acceptable salt or hydrate thereof where:

$R^1$ is H;

$R^2$ is a substituted or unsubstituted $(C_6-C_8)$alkyl, $(C_3-C_9)$ cycloalkyl, $(C_3-C_9)$ cycloalkyl $(C_1-C_8)$ alkyl), $(C_3-C_9)$ aryl, $(C_3-C_9)$aryl$(C_1-C_8)$alkyl, $(C_3-C_9)$heteroaryl, $(C_3-C_9)$heteroaryl$(C_1-C_8)$ alkyl, $(C_1-C_8)$hydroxyalkyl, $(C_3-C_9)$heterocyclyl, $(C_3-C_9)$heterocyclyl $(C_1-C_8)$ alkyl, $(C_1-C_8)$alkyl$(C_3-C_9)$aryl,$(C_1-C_8)$alkylamine, $(C_1-C_8)$alkylamide; or $R^1$ and $R^2$ taken together with the nitrogen to which they are attached form a substituted or unsubstituted $(C_3-C_9)$ heterocyclyl or heteroaryl;

$R^3$ is independently selected from the group consisting of $(C_1-C_8)$alkyl, halo, $(C_1-C_8)$alkoxy, $(C_1-C_8)$ alkyl-$SO_2$—, cyano, and $(C_1-C_8)$alkylC(=O)—;

n is an integer from 1–5;

wherein "substituted" refers to one or more substitutions with a substituent selected from the group consisting of cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, —O—$(C_1-C_6)$alkyl, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl.

17. The compound 3-amino-6-phenyl-pyrazine-2-carboxylic acid benzylamide.

18. A pharmaceutical composition comprising a compound of any one of claims 1–11 and a pharmaceutically acceptable carrier.

* * * * *